United States Patent [19]

Drent

[11] Patent Number: 4,789,756

[45] Date of Patent: Dec. 6, 1988

[54] PROCESS FOR THE PREPARATION OF AN ESTER OF A 3-ARYL-SUBSTITUTED ACRYLIC ACID

[75] Inventor: Eit Drent, Amsterdam, Netherlands

[73] Assignee: Shell Oil Company, Houston, Tex.

[21] Appl. No.: 141,181

[22] Filed: Jan. 6, 1988

[30] Foreign Application Priority Data

Jan. 20, 1987 [GB] United Kingdom ............... 8701198

[51] Int. Cl.$^4$ ............................................. C07C 69/76
[52] U.S. Cl. ................................. 560/104; 560/207; 562/406
[58] Field of Search ............... 560/104, 207; 562/406

[56] References Cited

U.S. PATENT DOCUMENTS

| | | | |
|---|---|---|---|
| 3,076,032 | 1/1963 | Riemenschneider et al. | 260/597 |
| 3,381,030 | 4/1968 | Biale et al. | 562/406 |
| 3,530,168 | 9/1970 | Biale | 260/486 |
| 3,759,984 | 9/1973 | Fujii et al. | 260/485 |
| 4,281,174 | 7/1981 | Current | 560/204 |
| 4,379,939 | 4/1983 | Radel et al. | 560/193 |
| 4,578,507 | 3/1986 | Wada et al. | 560/104 |
| 4,620,027 | 10/1986 | Hsu | 560/104 |
| 4,661,620 | 4/1987 | Takaki et al. | 562/406 |

FOREIGN PATENT DOCUMENTS

| | | |
|---|---|---|
| 0152075 | 8/1985 | European Pat. Off. . |
| 0177354 | 4/1986 | European Pat. Off. . |
| 50-00645 | 1/1975 | Japan . |
| 7021342 | 2/1982 | Japan . |
| 2126152 | 6/1987 | Japan . |

*Primary Examiner*—Paul J. Killos

[57] ABSTRACT

Process for the preparation of an ester of a 3-aryl-substituted acrylic acid by reacting (a) an aromatic hydrocarbon having one aliphatic carbon atom less than said 3-aryl-substituted acrylic acid and carrying a 1-alkenyl substituent, (b) carbon monoxide and (c) an alcohol in the presence of a Group VIII noble metal or a compound thereof, a quinone and a redox agent.

30 Claims, No Drawings

PROCESS FOR THE PREPARATION OF AN ESTER OF A 3-ARYL-SUBSTITUTED ACRYLIC ACID

FIELD OF THE INVENTION

The invention relates to a process for the preparation of an ester of a 3-aryl-substituted acrylic acid.

BACKGROUND OF THE INVENTION

It is known from U.S. Pat. No. 3,530,168 to contact an olefin, carbon monoxide and oxygen with an alcoholic solution of a catalyst comprising a Group VIII noble metal, a biphyllic ligand and a redox agent, to prepare mono- and diesters of saturated and unsaturated carboxylic acids having one more carbon atom than the olefin reactant. The examples in this patent show that esters of monocarboxylic acids were obtained in a relatively low yield, calculated on starting olefin.

According to the non pre-published British Patent Application No. 8602177, an optionally substituted ethylenically unsaturated hydrocarbon is reacted with carbon monoxide and an alcohol in the presence of a catalyst comprising a Group VIII noble metal, a quinone and a redox agent, to prepare diesters of dicarboxylic acids. This process is preferably carried out at a pressure in the range of from 5 to 200 bar, so as to obtain said diesters in a very high yield.

It has now been found that by using special starting ethylenically unsaturated hydrocarbons at a relatively low partial pressure of carbon monoxide, esters of mono-carboxylic acids are obtained in a high yield.

SUMMARY OF THE INVENTION

This invention provides a process for the preparation of an ester of a 3-aryl-substituted acrylic acid which process comprises reacting (a) an aromatic hydrocarbon containing a 1-alkenyl group with one or two hydrogen atoms in beta-position, (b) carbon monoxide and (c) an alcohol, at a partial pressure of carbon monoxide below 10 bar, in the presence of:

(1) a noble metal of Group VIII of the Periodic Table of the Elements and/or a compound thereof,
(2) a quinone, and
(3) a redox agent, and isolating said ester from the reaction mixture thus obtained.

DESCRIPTION OF THE PREFERRED EMBODIMENTS

The process according to the present invention is carried out at a partial pressure of carbon monoxide which is below about 10 bar so as to insure a high yield of esters of 3-aryl-substituted acrylic acids. This partial pressure is preferably between about 0.1 and about 4.5 bar.

The noble metals which are used in the process according to the present invention are platinum, rhodium, ruthenium, palladium, iridium and/or osmium. These metals may be used in metallic form or as compounds. Mixtures of compounds of the same or different such noble metals or mixtures of such noble metals in metallic form may be used. The noble metals may be used as finely divided metals, not supported on a carrier, or supported on a carrier, for example on activated carbon, pumice or graphite. The present process is preferably carried out in the presence of palladium and/or a compound of palladium. Very good results have been obtained with compounds of palladium. Examples of suitable compounds of Group VIII noble metals are salts, such as nitrates, sulfates, halides, (fluorides, chlorides, bromides and iodides) and carboxylates. Among the carboxylates salts of alkanoic acids having not more than 12 carbon atoms per molecule are preferred, particularly the Pd (II) salts. Palladium (II) acetate is most preferred.

Further examples of suitable palladium compounds are palladium complexes such as bis(2,4-pentanedionato)palladium, bis(picolinato)palladium, tetrakis(triphenylphosphine)palladium, tris(dibenzylideneacetone)dipalladium, bis(triphenylphosphine)(1,4-benzoquinone)palladium, tetrakisacetonitrilepalladium tetrafluoroborate, bis(tri-o-tolylphosphine)palladium acetate, bis(triphenylphosphine)palladium sulfate, palladium olefin complexes, for instance di-μ-chloro-dichlorobis(ethylene)dipalladium([Pd.C$_2$H$_4$.Cl$_2$]$_2$), and di-μ-chlorodichlorobis(propylene)dipalladium([Pd.C$_3$H$_6$.Cl$_2$]$_2$), and palladiumhydride complexes. Palladium may be used in complex combination with phosphites, such as triphenyl phosphite or tributyl phosphite.

The quinone applied in the process according to the present invention may be an ortho-quinone or a para-quinone and may be, for example, a benzoquinone, a naphthoquinone, an anthraquinone or a chrysenequinone. Preference is given to substituted or unsubstituted benzoquinones, particularly to p-benzoquinones. According to a preferred embodiment of the present invention halogen-substituted p-benzoquinones are present and very high yields of diesters of dicarboxylic acids are obtained. In this embodiment one or more fluorine, chlorine, bromine and/or iodine atoms are attached to the aromatic nucleus of the p-benzoquinone. Examples of such quinones are 2-iodo-, 2-bromo-, 2-chloro- and 2-fluoro-p-benzoquinone, 2,6-diiodo-, 2,6-dibromo-, 2,6-dichloro- and 2,6-difluoro-p-benzoquinone, 2,3,6-triiodo-, 2,3,6-tribromo-, 2,3,6-trichloro- and 2,3,6-trifluoro-p-benzoquinone. Tetrahalo-p-benzoquinones are preferred, particularly tetrachloro-p-benzoquinone (also referred to as "chloranil"). According to another preferred embodiment, unsubstituted p-benzoquinone is applied in the present process. Further examples of suitable quinones are 9,10-anthraquinone, 1,4-naphthoquinone, 5,6-chrysenequinone and alkyl-substituted p-benzoquinones such as 2-methyl-p-benzoquinone and 2,6-dimethyl-p-benzodquinone. Mixtures of quinones may be present, for example of p-benzoquinone and a halogen-substituted p-benzoquinone.

Redox agents are well known in the art. It is generally a compound of copper, iron, vanadium, cobalt or manganese. Mixtures of such compounds may be used. These five metals are preferably used in the form of salts of acids having a pKa below about 2.0, measured in aqueous solution at a temperature of about 25° C., such as chlorides, nitrates, sulfates, perchlorates and sulfonates, for example benzenesulfonates and p-tosylates. Other examples of suitable salts are carboxylates, preferably alkanoates and, more preferably, those alkanoates having not more than about 12 carbon atoms per molecule. Among the metal compounds cupric compounds are preferred, particularly cupric tosylate and cupric perchlorate. Further examples of suitable redox agents are cobalt(II) complexes of organic ligands, cupric acetate, cupric butyrate, cupric chloride, cupric bromide, ferrous propionate, ferric acetate, ferric chloride, ferric bromide, cobalt(II) acetate and manganese chloride.

The process according to the present invention may be carried out using a molar ratio noble metal of Group VIII and/or a compound thereof to aromatic hydrocarbon which is not critical and may vary within wide ranges. This molar ratio is suitably in the range of from about $10^{-2}$ to about $10^{-6}$.

The process according to the present invention may be carried out using a molar ratio redox agent to noble metal of Group VIII and/or a compound thereof which is not critical and may vary within wide ranges. This molav ratio is suitably in the range of from about 0.5 to about 1000 and preferably from about 1 to about 200.

The process according to the present invention results in the formation of an ester of a 3-aryl-substituted acrylic acid and of a hydroquinone. The hydroquinone may be isolated from the reaction mixture and, if desired, purified. The isolated and optionally purified hydroquinone may be used for any suitable purpose but is preferably oxidized in a suitable manner to the corresponding quinone which quinone is preferably used in the process according to the present invention.

It has, furthermore, been found that the yield of esters of 3-aryl-substituted acrylic acids is further enhanced by carrying out the process in the presence of molecular oxygen. The molecular oxygen may be supplied, for example, as pure oxygen, in air enriched with oxygen, in air or diluted with an inert gas such as argon. The oxygen is supplied using a molar ratio molecular oxygen to carbon monoxide which is not critical and may vary within wide ranges, preferably in the range of from about 1:3 to about 1:6, the stoichiometric ratio being about 1:4. The oxygen may be supplied in one portion but may, for safety reasons, be supplied in two or more than two portions.

The process according to the present invention can be carried out using a molar ratio quinone to aromatic hydrocarbon which is not critical and which may vary within wide limits. This molar ratio may vary, for example, in the range of from about 0.001 to about 5.

The process according to the present invention can be carried out using a molar ratio carbon monoxide to aromatic hydrocarbon which is not critical and may vary within wide limits, preferably in the range of from about 0.5:1 to about 10:1 and particularly from about 1:1 to about 3:1, the stoichiometric ratio being 2.

The process according to the present invention can be carried out in wide ranges of temperature, preferably in the range of from about 20° C. to about 200° C., more preferably from about 50° C. to about 125° C.

The alcohol can be applied in a molar ratio alcohol to aromatic hydrocarbon which is not critical and may vary within wide limits. This molar ratio is suitably at least the stoichiometric molar ratio which is 1 and may be, if desired, in the range of from 1 to about 1000.

The process according to the present invention can be carried out in the absence or, which is preferred, in the presence of a solvent which does not inhibit the reaction. The alcohol which is used as a reactant may be used as a solvent. Very good results have been obtained with ethers. Examples of ethers are methyl ethyl ether, diethyl ether, dipropyl ether, tetrahydrofuran, dimethyl ether of diethylene glycol (also referred to as "diglyme"), methyl tert-butyl ether, dichloroethyl ether, ethyl phenyl ether, diethylene glycol diethyl ether and 1,4-dioxane. Other examples of suitable solvents are halogenated hydrocarbons such as chloroform, chlorobenzene, carbon tetrachloride and perfluoroalkanes; esters such as the methyl and ethyl esters of formic acid, acetic acid, adipic acid, succinic acid, propionic acid, oxalic acid and benzoic acid; sulfones such as dimethyl sulfone, methyl butyl sulfone and tetrahydrothiophone 1,1-dioxide (also referred to as "sulfolane"); aromatic hydrocarbons such as benzene, toluene and the three xylenes; cycloalkanes such as cyclohexane; nitrobenzene.

The aryl group in the starting aromatic hydrocarbon may be, for example, monocyclic, which is preferred, or fused polycyclic. In the former case, the aryl group is derived from benzene. In the latter case, the aryl group may be derived from, for example, indene, naphthalene, anthracene, phenanthrene, fluorene or picene. As used herein, the term "aromatic hydrocarbon" refers to aromatic hydrocarbons which do and do not carry substituents other than the 1-alkenyl group. Examples of suitable aromatic hydrocarbon substituents other than the 1-alkenyl group include alkyl groups, preferably those having not more than five carbon atoms, and halogen atoms, viz. fluorine, chlorine, bromine and iodine atoms.

The carbon atoms in the 1-alkenyl substituent having the alpha- and beta-positions with respect to the aromatic nucleus each may carry one substituent, preferably an alkyl group having less than five carbon atoms. Preferably, the 1-alkenyl group is an unsubstituted vinyl group, the starting aromatic hydrocarbon being styrene. Other examples of aromatic hydrocarbons are β-methylstyrene, β-pentylstyrene, p-methylstyrene, p-methoxystyrene, p-chlorostyrene and β-methyl-p-isopropylstyrene.

A wide variety of alchols may be used in the process according to the present invention; the alcohol may be mono- or polyhydric, may be primary, secondary or tertiary and may be aliphatic, cycloaliphatic or aromatic. Monohydric alcohols having in the range of from 1 to about 20 carbon atoms per molecule and, particularly, alkanols, are preferred. Very good results have been obtained with methanol. Other examples of suitable alcohols are ethanol, propanol, 2-propanol, butanol, tert-butyl alcohol, pentanol, hexanol, heptanol, octanol, nonanol, decanol, ethylene glycol, diethylene glycol, propylene glycol, ethylene glycol monoalkyl ethers (the alkyl group having up to, for example, 10 carbon atoms), 1,3-butanediol, cyclohexanol, phenol, benzyl alcohol, 2-naphthol and 2-phenanthrol. Compounds which can decompose during the reaction and liberate alcohols may be applied, for example acetals, ketals, carboxylic acid orthoesters and orthoboric acid esters.

The process according to the present invention is an example of the so-called "oxidative carbonylation". The acid portion of the ester obtained according to the present invention is derived from the aromatic hydrocarbon and the alcohol portion of the ester is derived from the alcohol. Accordingly, styrene, methanol and carbon monoxide are converted into methyl cinnamate, α-methylstyrene, ethanol and carbon monoxide into ethyl β-methylcinnamate; 1-propenylbenzene, methanol and carbon monoxide into methyl β-methylcinnamate, and 1-butenylbenzene, methanol and carbon monoxide into methyl β-ethylcinnamate. The process according to the present invention is particularly important for the preparation of methyl cinnamate which is a precursor of perfumes, agricultural chemicals and sweeteners.

The process according to the invention can be carried out batchwise, semi-continuously or continuously. The reaction time varies in relation to the temperature used and is usually between about 0.5 and about 20 hours.

The ester of a 3-aryl-substituted acrylic acid obtained by the process according to the present invention may be isolated by conventional separating means, such as distillation or extraction.

The following Examples illustrate the invention and are not intended to be construed as limiting the invention.

EXAMPLES 1–5

The experiments described below were carried out in a 300 ml autoclave made of Hastelloy C ("Hastelloy" is a trade name) provided with a magnetically driven stirrer. In each experiment the autoclave was charged with palladium(II) acetate (0.1 mmol), methanol (10 ml, 247 mmol), diglyme (50 ml) and styrene (15 ml, 131 mmol). The autoclave was further charged with chloranil and a redox agent as detailed in the Table hereinafter, flushed with carbon monoxide, charged with carbon monoxide until a partial pressure thereof of 5 bar was obtained, heated to a temperature of 100° C. and kept at this temperature for two hours. The partial pressure of carbon monoxide was kept constant at a value of 5 bar during this period. After cooling to ambient temperature the conversion of styrene and the selectivity to methyl cinnamate were determined. This selectivity is defined as 100xa:b, in which "a" is the amount of styrene that has been converted into methyl cinnamate and "b" is the total amount of styrene that has been converted.

TABLE

| Example | Chloranil mmol | Redox agent mmol | Conversion of styrene, % | Selectivity to methyl cinnamate, % | Yield of methyl cinnamate, calculated on chloranil, % |
|---|---|---|---|---|---|
| 1 | 50 | Cu(tosylate)$_2$ 1 | 42 | 80 | 88 |
| 2 | 100 | Cu(tosylate)$_2$ 1 | 55 | 85 | 61 |
| 3 | 50 | CuCl$_2$ 1 | 55 | 60 | 86 |
| 4 | 50 | CuBr$_2$ 1 | 50 | 75 | 98 |
| 5 | 50 | MnCl$_2$ 1 | 45 | 75 | 88 |

Among the by-products obtained in each of the Examples dimethyl phenylsuccinate was present in a very minor amount.

The results presented in the Table hereinbefore show that methyl cinnamate has been obtained in a very high yield.

COMPARATIVE EXPERIMENT A

The experiment of Example 1 was repeated with the exception that the partial pressure of carbon monoxide was 10 bar instead of 5 bar. The conversion of styrene, after 1 h, was 40% and the selectivity to methyl cinnamate was 45%, the yield of methyl cinnamate, calculated on chloranil, being 47%. Dimethyl phenylsuccinate was the main by-product.

COMPARATIVE EXPERIMENT B

Comparative Experiment A was repeated with the exception that the partial pressure of carbon monoxide was 20 bar instead of 10 bar. The conversion of styrene, after 1 hr, was 45% and the selectivity to methyl cinnamate was 31%, the yield of methyl cinnamate, calculated on chloranil, being 37%. Dimethyl phenylsuccinate was the main by-product.

COMPARATIVE EXPERIMENT C

The experiment of Example 1 was repeated with the exception that no redox agent was present. The conversion of styrene, after 2 h, was 50% and the selectivity to methyl cinnamate was only 55%, and yield of methyl cinnamate, calculated on chloroanil, being 72%. Methyl 3-phenylpropionate was the main by-product.

What is claimed is:

1. A process for the preparation of an ester of a 3-aryl-substituted acrylic acid which comprises reacting (a) an aromatic hydrocarbon containing a 1-alkenyl group with at least one hydrogen atom in beta-position, (b) carbon monoxide and (c) an alcohol, at a partial pressure of carbon monoxide below about 10 bar, in the presence of:
   (1) a noble metal selected from the group consisting of Group VIII of the Periodic Table of the Elements, a compound of a Group VIII metal, and mixtures thereof,
   (2) a quinone, and
   (3) a redox agent,
and isolating said ester from the reaction mixture thus obtained.

2. The process of claim 1 wherein said process is carried out in the presence of palladium and/or a compound of palladium.

3. the process of claim 1 wherein said process is carried out in the presence of a palladium compound.

4. The process of claim 3 wherein said palladium compound is a Pd(II) salt of an alkanoic acid having not more than about 12 carbon atoms per molecule.

5. The process of claim 4 wherein said palladium compound is palladium(II) acetate.

6. The process of claim 1 wherein said quinone is a substituted or an unsubstituted benzoquinone.

7. The process of claim 6 wherein said quinone is a p-benzoquinone.

8. The process of claim 7 wherein said p-benzoquinone is a halogen-substituted p-benzoquinone.

9. The process of claim 8 wherein said p-benzoquinone is tetrachloro-p-benzoquinone.

10. The process of claim 7 wherein said p-benzoquinone is unsubstituted p-benzoquinone.

11. The process of claim 1 wherein said redox agent is selected from the group consisting of a compound of copper, a compound of iron, a compound of vanadium, a compound of cobalt, a compound of manganese and mixtures thereof.

12. The process of claim 11 wherein said redox agent is a salt of an acid having a pKa below 2.0, measured in aqueous solution at a temperature of 25° C.

13. The process of claim 11 wherein said redox agent is a cupric compound.

14. The process of claim 13 wherein said cupric compound is cupric tosylate.

15. The process of claim 12 wherein said redox agent is ferrous perchlorate.

16. The process of claim 1 wherein a molar ratio noble metal of Group VIII and/or a compound of a Group VIII metal to aromatic hydrocarbon in the range of from about $10^{-2}$ to about $10^{-6}$ is used.

17. The process of claim 1 wherein a molar ratio redox agent to noble metal of Group VIII and/or a compound of a Group VIII metal in the range of from about 1 to about 200 is used.

18. The process of claim 1 wherein said process is carried out in the presence of molecular oxygen.

19. The process of claim 18 wherein a molar ratio molecular oxygen to carbon monoxide in the range of from about 1:3 to about 1:6 is used.

20. The process of claim 1 wherein a molar ratio carbon monoxide to aromatic hydrocarbon in the range of from about 0.5:1 to about 10:1 is used.

21. The process of claim 20 wherein said molar ratio is in the range of from about 1:1 to about 3:1.

22. The process of claim 1 wherein said process is carried out in the presence of a solvent.

23. The process of claim 22 wherein said solvent is an ether.

24. The process of claim 1 wherein a partial pressure of carbon monoxide is maintained between about 0.5 and about 4.5 bar.

25. The process of claim 1 wherein a temperature is maintained in the range of from about 20° C. to about 200° C.

26. The process of claim 1 wherein said aromatic hydrocarbon is monocyclic and said 1-alkenyl substituent is a vinyl group.

27. The process of claim 26 wherein said aromatic hydrocarbon is styrene.

28. The process of claim 1 wherein said alcohol is monohydric and has in the range of from about 1 to about 20 carbon atoms per molecule.

29. The process of claim 28 wherein said alcohol is an alkanol.

30. The process of claim 29 wherein said alkanol is methanol.

* * * * *